United States Patent
Lee et al.

(10) Patent No.: US 10,299,482 B2
(45) Date of Patent: *May 28, 2019

(54) METHODS FOR THE CONTROL OF ARTHROPODS USING NEAR-IDEAL GAS PHASE HYDROGEN PEROXIDE

(71) Applicant: Synexis LLC, Kansas City, MO (US)

(72) Inventors: James D. Lee, Kansas City, MO (US); Douglas J. Bosma, Kansas City, MO (US)

(73) Assignee: Synexis LLC, Kansas City, MO (US)

( * ) Notice: Subject to any disclaimer, the term of this patent is extended or adjusted under 35 U.S.C. 154(b) by 41 days.

This patent is subject to a terminal disclaimer.

(21) Appl. No.: 15/727,617

(22) Filed: Oct. 8, 2017

(65) Prior Publication Data

US 2018/0027817 A1 Feb. 1, 2018

Related U.S. Application Data

(63) Continuation of application No. 14/891,238, filed as application No. PCT/US2014/038652 on May 19, 2014, now Pat. No. 9,808,013.

(60) Provisional application No. 61/824,689, filed on May 17, 2013.

(51) Int. Cl.
| | | |
|---|---|---|
| *A01N 59/00* | (2006.01) | |
| *A23L 3/00* | (2006.01) | |
| *A23L 3/3409* | (2006.01) | |
| *A23L 3/3445* | (2006.01) | |
| *A01M 1/20* | (2006.01) | |

(52) U.S. Cl.
CPC .......... *A01N 59/00* (2013.01); *A01M 1/2022* (2013.01); *A23L 3/00* (2013.01); *A23L 3/3409* (2013.01); *A23L 3/3445* (2013.01)

(58) Field of Classification Search
CPC .... A01N 59/00; A01M 1/2022; A23L 3/3445; A23L 3/3409; A23L 3/00
USPC ...................................................... 424/616
See application file for complete search history.

(56) References Cited

U.S. PATENT DOCUMENTS

| | | | |
|---|---|---|---|
| 6,455,075 B1 | 9/2002 | Larose | |
| 8,168,122 B2 * | 5/2012 | Lee | ............. A61L 2/208 |
| | | | 422/120 |
| 8,685,329 B2 | 4/2014 | Lee | |
| 2006/0269438 A1 | 11/2006 | Lagunas-Solar et al. | |
| 2009/0263499 A1 | 10/2009 | Platt, Jr. et al. | |
| 2012/0183444 A1 | 7/2012 | Lee | |

FOREIGN PATENT DOCUMENTS

| | | |
|---|---|---|
| JP | H07-170897 | 7/1995 |
| JP | 2009-254832 | 11/2009 |
| JP | 2010-535807 | 11/2010 |
| JP | 2012-517862 | 8/2012 |
| WO | WO 2009/021108 A1 | 2/2009 |
| WO | WO 2010/093796 A1 | 8/2010 |
| WO | WO 2012/031365 A1 | 3/2012 |
| WO | WO 2015/171633 A1 | 11/2015 |

OTHER PUBLICATIONS

U.S. Appl. No. 61/988,535, filed May 5, 2014, Lee.
International Search Report dated Aug. 26, 2014, in International Patent Application No. PCT/US2014/038652.
Notification of Reasons for Refusal dated Feb. 20, 2018 in Japanese Application No. JP2016-514163.

\* cited by examiner

*Primary Examiner* — Yanzhi Zhang

(74) *Attorney, Agent, or Firm* — Arnold & Porter Kaye Scholer

(57) ABSTRACT

The present disclosure relates to methods and devices for controlling arthropods, including insects and arachnids in an environment. The methods generally comprise: generating a near-ideal gas Purified Hydrogen Peroxide Gas (PHPG) that is substantially non-hydrated (e.g., in the form of water in solution or water in solution or water molecules bonded by covalence, van der Waals forces, or London forces) and substantially free of, e.g., ozone, plasma species, and/or organic species; and directing the gas comprising primarily PHPG into the environment such that the PHPG acts to control arachnids in the environment. In certain aspects, the arachnids may be totally or partially killed.

19 Claims, No Drawings

METHODS FOR THE CONTROL OF ARTHROPODS USING NEAR-IDEAL GAS PHASE HYDROGEN PEROXIDE

CROSS-REFERENCE TO RELATED APPLICATIONS

This application is a continuation application of U.S. application Ser. No. 14/891,238, filed Nov. 13, 2015, which is a national stage application of International Application No. PCT/US2014/038652 filed May 19, 2014, which claims priority to U.S. Provisional Application No. 61/824,689 filed May 17, 2013, which is herein incorporated by reference in its entirety.

FIELD OF THE DISCLOSURE

The present disclosure relates generally to methods for the control of arthropods, including insects and arachnids. In certain aspects, photocatalytic processes may be utilized to form near-ideal gas phase hydrogen peroxide for use in the methods described herein.

BACKGROUND

As described herein, in certain aspects of the disclosure, hydrogen peroxide may be produced as a near-ideal gas phase, purified hydrogen peroxide gas (PHPG). In this form hydrogen peroxide behaves, in all respects, as a near-ideal gas and is not hydrated, or otherwise combined with water when produced.

The fundamental nature of a photocatalytic process is to create active intermediates in a chemical reaction by absorption of light. This occurs when a photon of the appropriate wavelength strikes the photocatalyst. The energy of the photon is imparted to a valence band electron, promoting the electron to the conduction band, thus leaving a "hole" in the valence band. In the absence of an adsorbed chemical species, the promoted electron will decay and recombine with the valence band hole. Recombination is prevented when the valence band hole captures an electron from an oxidizable species—preferentially molecular water—adsorbed to an active surface site on the photocatalyst. Concurrently, a reducible species adsorbed on the catalyst surface—preferentially molecular oxygen—may capture a conduction band electron.

Upon initiation of the photocatalytic process, or at the entrance point of a photocatalytic plasma reactor, the following reactions occur.

Oxidation $$2\text{ photons} + 2H_2O \rightarrow 2OH^* + 2H^+ + 2e^-$$

$$2OH^* \rightarrow H_2O_2$$

Reduction $$O_2 \pm 2H^+ + 2e^- \rightarrow H_2O_2$$

Once hydrogen peroxide has been produced, however, the photocatalyst preferentially reduces hydrogen peroxide (reduction potential 0.71 eV) instead of molecular oxygen (reduction potential −0.13 eV), and the reaction shifts to the following equilibrium which takes place within the majority of the plasma reactor volume.

Oxidation $$2\text{ photons} + 2H_2O \rightarrow 2OH^* + 2H^+ + 2e^-$$

$$2OH^* \rightarrow H_2O_2$$

Reduction $$H_2O_2 + 2H^+ + 2e^- \rightarrow 2H_2O$$

In the context of the present disclosure, near-ideal gas Purified Hydrogen Peroxide Gas (PHPG) may be produced using a photocatalytic process with a purpose-designed morphology that enables the removal of near-ideal gas phase hydrogen peroxide from the PHPG reactor before it is forced to undergo subsequent reduction by the photocatalyst. Denied ready availability of adsorbed hydrogen peroxide gas, the photocatalyst is then forced to preferentially reduce oxygen, rather than hydrogen peroxide. Hydrogen peroxide gas may then generally be produced simultaneously by both the oxidation of water and the reduction of dioxygen in the photocatalytic process. Without intending to be limited, in operation the amount of hydrogen peroxide produced may be doubled, then removed from the system before the vast majority of it can be reduced—thereby resulting in an output of near-ideal gas PHPG that is thousands of times greater than the incidental output of unpurified hydrogen peroxide from an equal number of active catalyst sites within a photocatalytic plasma reactor under the same conditions. This purpose-designed morphology also enables the production of near-ideal gas PHPG at absolute humidities well below those at which a photocatalytic plasma reactor can effectively operate. For example, near-ideal gas PHPG outputs greater than 5.0 ppm have been achieved at an absolute humidity of 2.5 milligrams per Liter. In the purpose-designed morphology the dominant reactions become:

Oxidation $$2\text{ photons} + 2H_2O \rightarrow 2OH^* + 2H^+ + 2e^-$$

$$2OH^* \rightarrow H_2O_2$$

Reduction $$O_2 \pm 2H^+ + 2e^- \rightarrow H_2O_2$$

However, without being limited by theory, it should be noted that methods and devices of the present disclosure are not achieved as a result of the photocatalytic process, but by the effects of near-ideal gas PHPG once it is released into the environment.

Using morphology that permits immediate removal of hydrogen peroxide gas before it can be reduced, near-ideal gas PHPG may be generated in any suitable manner known in the art, including but not limited to, any suitable process known in the art that simultaneously oxidizes water in gas form and reduces oxygen gas, including gas phase photocatalysis, e.g., using a metal catalyst such as titanium dioxide, zirconium oxide, titanium dioxide doped with cocatalysts (such as copper, rhodium, silver, platinum, gold, etc.), or other suitable metal oxide photocatalysts. Near-ideal gas PHPG may also be produced by electrolytic processes using anodes and cathodes made from any suitable metal, or constructed from metal oxide ceramics using morphology that permits immediate removal of hydrogen peroxide gas before it can be reduced. Alternatively, near-ideal gas PHPG may be produced by high frequency excitation of gaseous water and oxygen molecules on a suitable supporting substrate using morphology that permits immediate removal of hydrogen peroxide gas before it can be reduced.

As a near-ideal gas, hydrogen peroxide is not appreciably lighter than or heavier than air, having a molar mass of 34.0148 grams per mole. Near-ideal gas phase hydrogen peroxide diffuses through air as any other near-ideal gas would, and passes through air-permeable materials, unhindered by the surface tension of water as is seen in the behavior of micro-droplets comprising aqueous phase vapor forms of hydrogen peroxide often referred to as gaseous.

In this form, near-ideal gas phase hydrogen peroxide can penetrate to any space that can be reached by air itself. This includes all areas in which arachnids and insects are present in a room, such as crevices between materials, inside air-permeable cushions and in air-permeable bedding.

Continuously produced via a PHPG diffuser device, as discussed herein, an equilibrium concentration above 0.04 parts per million of near-ideal gas phase hydrogen peroxide may be achieved and maintained continuously in an environment. At equilibrium at one atmosphere pressure and 19.51 degrees Celsius, near-ideal gas phase hydrogen peroxide will be present in every cubic micron of air at an average amount of one molecule per cubic micron for each 0.04 parts per million of concentration. At one part per million, the average number of hydrogen peroxide molecules per cubic micron will be 25, and at 3.2 parts per million it will be 80.

Not to be limited by theory, near-ideal gas phase hydrogen peroxide will be "inhaled" or processed by arthropods including but not limited to arachnids and insects along with air, causing damage to sensitive tissues and either killing the arthropod or resulting in changes in behavior. In the case of arachnids, near-ideal gas phase hydrogen peroxide passes through tracheal tubes and body apertures to reach sensitive tissues and the book lungs of arachnids. The result of continuous exposure to near-ideal gas phase hydrogen peroxide at even low concentrations is damage to the tissues used in air exchange, and the death of the arachnid. Most arthropods, including insects do not have lungs, but survive solely by distributing oxygen through the body by means of a network of tracheal tubes. By this means near-ideal gas phase hydrogen peroxide reaches every portion of an arthropod's body and causes death to the arthropod, such as an insect. Not to be limited by theory the near-ideal gas phase hydrogen peroxide damages their air exchange tissues.

By contrast, humans and other vertebrates have respiratory mechanisms that protect them from equivalent concentrations of near-ideal gas phase hydrogen peroxide. Human lungs produce hydrogen peroxide at high rates and a cubic micron of human lung secretion contains an equilibrium concentration of between 600 molecules, and 60,000 molecules of hydrogen peroxide in aqueous phase, along with enzymes that consume hydrogen peroxide and regulate its concentration. Enzymes such as lactoperoxidase and catalase which perform this function are known to have enzymatic velocities of thousands of molecular reactions per second.

In one aspect of the present disclosure, a method of controlling an arthropods, such as insects or arachnids, in an environment is disclosed. In certain aspects, the arthropods are part of a population or a plurality of populations. In certain aspects, an arthropod, insect, or arachnid population is totally or partially killed. The method generally comprises (a) generating a near-ideal gas comprised of Purified Hydrogen Peroxide Gas (PHPG) that is substantially free of, e.g., hydration (i.e., non-hydrated, in the form of water in solution or water molecules bonded by covalence, van der Waals forces, or London forces), ozone, plasma species, and/or organic species; and (b) directing the gas comprised of PHPG into the environment such that the PHPG controls arthropod, insect, or arachnid populations in the environment.

As used herein, the term "Purified Hydrogen Peroxide Gas" or PHPG generally means a gas form of hydrogen peroxide that is substantially free of at least hydration (in the form of water in solution or water molecules bonded by covalence, van der Waals forces, or London forces) and substantially free of ozone.

In accordance with the present disclosure, the terms "substantial absence of ozone" "substantially free of ozone", etc., generally mean amounts of ozone below about 0.015 ppm, down to levels below the LOD (level of detection) for ozone. Such levels are below the generally accepted limits for human health. In this regard, the Food and Drug Administration (FDA) requires ozone output of indoor medical devices to be no more than 0.05 ppm of ozone. The Occupational Safety and Health Administration (OSHA) requires that workers not be exposed to an average concentration of more than 0.10 ppm of ozone for 8 hours. The National Institute of Occupational Safety and Health (NIOSH) recommends an upper limit of 0.10 ppm of ozone, not to be exceeded at any time. Environmental Protection Agency's (EPA's) National Ambient Air Quality Standard for ozone is a maximum 8 hour average outdoor concentration of 0.08 ppm. The diffuser devices described herein have consistently demonstrated that they do not produce ozone at levels detectable by means of a Draeger Tube.

In certain aspects, the method comprises (a) exposing a metal, or metal oxide, catalyst to ultraviolet light in the presence of humid purified ambient air under conditions so as to form near-ideal gas Purified Hydrogen Peroxide Gas (PHPG) that is substantially free of at least one of hydration (in the form of water in solution or water molecules bonded by covalence, van der Waals forces, or London forces), ozone, plasma species, and organic species; and (b) directing the PHPG into the environment such that the PHPG controls arthropods in the environment.

In one aspect, the ultraviolet light produces at least one wavelength in a range above about 181 nm, above about 185 nm, above about 187 nm, between about 182 nm and about 254 nm, between about 187 nm and about 250 nm, between about 188 nm and about 249 nm, between about 255 nm and about 380 nm, etc. In certain aspects, wavelengths between about 255 nm and 380 nm may be preferred to improve yields of PHPG.

In certain aspects, the amount of PHPG may vary from about 0.005 ppm to about 5.0 ppm, more particularly, from about 0.02 ppm to about 1.5 ppm, in the environment. In certain aspects, the amount of PHPG may vary from about 0.5 ppm to about 1.5 ppm. PHPG levels of 1.5 ppm using a feed of untreated air containing absolute humidity as low as 3.5 mg/L can consistently be achieved. More particularly, PHPG levels from about 0.09 ppm to about 5.0 ppm using humid re-circulated air, can be produced in the environment to be treated. Also provided for an included are methods of treating arthropod population comprising providing PHPG gas at between 0.4 to 1.0 ppm. In another aspect, PHPG may be provided at between 0.5 to 1.5 ppm for the control of arthropods. In certain embodiments, the level of PHPG is maintained at 1.0 ppm or less.

In certain aspects of the present disclosure, the humidity of the ambient air is preferably above about 1% relative humidity (RH), above about 5% RH, above about 10% RH, etc. In certain aspects, the humidity of the ambient air may be between about 10% and about 99% RH. In one aspect, the method of the present disclosure includes regulating the humidity of the ambient air within the range of about 5% to about 99% RH, or about 10 to about 99% RH.

A suitable diffuser device may be used to generate the near-ideal gas PHPG, such as those disclosed in WO/2009/021108 or WO/2010/093796, the contents of which are herein incorporated by reference in their entireties. The diffuser design may optimize near-ideal gas PHPG production by spreading the air permeable photocatalytic PHPG reactor surface thinly over a large area that is perpendicular to air flow (e.g., in certain aspects, over a sail-like area), rather than by compacting it into a volume-optimizing morphology designed to maximize residence time within the plasma reactor.

For example, by configuring the PHPG reactor morphology as a thin, sail-like air-permeable structure, just inside the diffuser's interior shell, the exit path length for hydrogen peroxide molecules produced on the catalyst becomes diminishingly short, and their residence time within the PHPG reactor structure is reduced to a fraction of a second, preventing the vast majority of hydrogen peroxide molecules from being subsequently adsorbed onto the catalyst and reduced back into water. Also, by placing the catalyst substrate just inside the interior surface of the diffuser shell, not only is PHPG reactor surface area maximized, but the near-ideal gas PHPG produced also passes out of the diffuser almost immediately and thus avoids photolysis from prolonged exposure to the UV light source. By means of this morphology, near-ideal gas PHPG output concentrations as high as 0.40 ppm may be achieved.

Generally, the present disclosure has been described in specific aspects with some degree of particularity, it is to be understood that this description has been given only by way of example and that numerous changes in the details of construction, fabrication and use, including the combination and arrangement of parts, may be made without departing from the spirit and scope of the present disclosure as shown in the following example aspects.

In previous disclosures, obstacles in the field to produce highly concentrated non-hydrated Purified Hydrogen Peroxide Gas, are overcome and the production of PHPG has many applications in domestic, industrial, and agricultural arenas. While conducting studies on the performance and PHPG output of a PHPG producing apparatus and its activity on molds, bacteria and viruses, the surprising and unexpected observation that near-ideal gas phase hydrogen peroxide can be used to kill, partially kill, or modify the behavior of most species of arthropods including insects and arachnids, among others. Without being limited by a particular theory, the surprising effects of PHPG gas on the behavior of many species of insects and arachnids may be due at least in part because many species of arthropods appear to have limited or no natural protection against hydrogen peroxide gas.

Surprisingly, the inventors also discovered that non-hydrated hydrogen peroxide gas acts as a repellant against arthropods including arachnids, flying insects, and crawling insects, causing them to flee an area protected by the hydrogen peroxide gas and preventing them from entering the area. Further, the inventors found that hydrogen peroxide gas causes many species of arthropods that are unable to flee a PHPG enriched area to become inactive and die over a period of time ranging from hours to days. The inventors also observed that hydrogen peroxide gas can interrupt the life cycle of many species of arthropods, even causing pupae, larvae, and nits to die. Based on these findings, the application of PHPG gas to arthropod control has a wide range of beneficial uses in the domestic, industrial and agricultural industries.

In addition to the broad effectiveness of PHPG for the control of arthropods, PHPG, used at concentrations below a few parts per million, acts as a "green" pesticide which breaks down into water and oxygen in the environment, leaving no toxic residue, and is not harmful to humans, pets, or plants.

SUMMARY

The present disclosure provides for, and includes, a method for controlling an arthropod in an environment comprising providing Purified Hydrogen Peroxide Gas (PHPG) to an environment to prepare a PHPG containing environment having PHPG gas at a final concentration of at least 0.05 parts per million and maintaining the PHPG containing environment for a time period sufficient to control an arthropod.

The present disclosure further provides for, and includes, a method of treating an animal for an arthropod parasite comprising placing an animal in a PHPG containing environment for a period of time.

The present disclosure further provides for, and includes, a method for controlling at least one insect or arachnid population in an environment, the comprising: (a) generating a gas comprising near-ideal gas Purified Hydrogen Peroxide Gas (PHPG) that is substantially non-hydrated and substantially free of ozone, plasma species, and optionally organic species; (b) directing the PHPG into the environment such that the hydrogen peroxide gas acts to control at least one insect or arachnid population in the environment.

In another aspect, the present disclosure provides for, and includes, a method of termite control comprising treating a termite infested house with PHPG.

In a further aspect, the present disclosure provides for, and includes, a method of controlling arthropods in a greenhouse comprising providing PHPG to a green house.

In an aspect, the present disclosure further provides for, and includes, a method of treating a houseplant for the control of an arthropod comprising placing an arthropod infested plant in a PHPG containing environment.

In another aspect, the present disclosure provides for a method for controlling an arthropod in an agricultural product during shipping comprising: providing Purified Hydrogen Peroxide Gas (PHPG) at a concentration of at least 0.05 parts per million to a shipping container containing agricultural produce to prepare a PHPG containing shipping container; shipping the PHPG containing shipping container; and maintaining the PHPG concentration during the shipping, wherein the arthropod is controlled.

In an aspect, the present disclosure provides for and includes a method for controlling an arthropod in a food processing facility comprising providing Purified Hydrogen Peroxide Gas (PHPG) at a concentration of at least 0.05 parts per million to a food processing facility.

DETAILED DESCRIPTION

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. For purposes of the present disclosure, the following terms are defined below.

As used herein, "a reduction" of a population of arthropods such as an insect population or arachnid population in an environment having PHPG means that the level is reduced relative to the numbers of organisms of a population in an environment lacking PHPG. In some aspects, a reduction may occur due to the death or incapacitation of an arthropod population or due to the exit of members of the population from the PHPG containing environment.

As used herein, the term "at least a partial reduction" of a population of arthropods such as an insect population or arachnid population in an environment having PHPG means that the level is reduced by at least 25% relative to the numbers of organisms of a population in an environment lacking PHPG. Also as used herein, it is understood that in environments having multiple populations of arthropods, each population may be "partially reduced" independently.

As used herein, the term "a substantial reduction" of a population of arthropods such as an insect population or arachnid population in an environment having PHPG means that the level is reduced by at least 75% relative to the numbers of organisms of a population in an environment lacking PHPG. Also as used herein, it is understood that in environments having multiple populations of arthropods, each population may be "substantially reduced" independently.

As used herein, the term "an effective elimination" of a population of arthropods such as an insect population or arachnid population in an environment having PHPG means that the level is reduced by greater than 95% relative to the numbers of organisms of a population in an environment lacking PHPG. Also as used herein, it is understood that in environments having multiple populations of arthropods, each population may be "effectively eliminated" independently. An effective amount of PHPG is preferably capable of providing at least a partial reduction, more preferably a substantial reduction, or most preferably effective elimination of an arthropod population.

As used herein, the terms "suppress," "repress," and "downregulate" when referring to a population of arthropods used equivalently herein and mean that the levels of a population of arthropods are reduced relative to the number of arthropods in a population that would occur in the absence of PHPG under similar or identical conditions.

As used herein, the terms "control," "controls," or "controlling" a population of arthropods by providing PHPG to the arthropod for a period of time refers to either the killing of the arthropod, induction of a behavioral change in the arthropod, or both, that results in reduction of the population of the arthropod in the PHPG environment relative to an untreated environment. As provided in detail below, different arthropod populations are controlled at different levels of PHPG and may require different periods of exposure to the PHPG environment to accomplish desired levels of reduction.

As used herein, the singular form "a," "an" and "the" include plural references unless the context clearly dictates otherwise. For example, the term "an arthropod" or "at least one arthropod" may include a plurality of arthropods, including mixtures thereof. Also as used herein, an arthropod includes and provides for a population of arthropods. As used herein, a population of arthropods may further include a mixed population of arthropods.

The present disclosure provides for an includes method for controlling an arthropod by providing PHPG to the arthropod for a period of time. An arthropod may be controlled in a variety of ways including by killing the arthropod at one or more stages of development or as an adult. In certain aspects, providing PHPG to an environment leads to the death of the arthropod after a period of time. In an aspect, providing PHPG gas provides for the death of a nymph stage of an arthropod. In an aspect, PHPG gas causes the death of an arthropod egg such that larvae never hatch. In an aspect, PHPG acts on adult stages of an arthropod. In some aspects, providing PHPG is an effective arthropodicide against all developmental stages of an arthropod species. As provided below, both the length of time necessary to kill the arthropod and the amount of PHGP necessary to kill the arthropod may vary depending on the species of the arthropod.

The present disclosure also includes and provides for methods of control which disrupt the behavior of the arthropod. In some aspects, the methods of control provide for both the disruption of arthropod behavior and provide arthropodicidal effects. In some aspects, after initial exposure to a concentration of PHPG, the arthropod ceases all activity and becomes immobile and dormant. In other aspects, exposure to a concentration of PHPG leads to enhanced activity of the arthropod. In certain aspects, the activity of flying arthropods greatly increases and can be characterized by high agitation and frantic activity. In aspects according to the present disclosure, control of an arthropod after exposure to PHPG includes disruption of normal mating behavior. Other behavioral changes observed in arthropods exposed to PHPG containing environments includes disorientation. In an aspect, the present methods included inducing disorientation in an arthropod species. In some aspects, disorientation leads to a loss of feeding behavior. In other aspects, disorientation leads to a loss of mating behavior.

In certain aspects according to the present disclosure, changes in behavior caused by exposure to PHPG may also be accompanied by physical signs of distress of the arthropod. In some aspects, physical signs of distress include regurgitation of recent meals. In another aspect, the arthropod may prematurely lay eggs. In certain aspects, the prematurely laid eggs may be fertilized eggs. In other aspects, the prematurely laid eggs may be un-fertilized. In aspects according the present disclosure, exposure to PHPG gas results in the death of the prematurely laid eggs.

Also provided and included in the present disclosure are methods of controlling larval forms of an arthropod. In certain aspects, providing a PHPG leads to the premature hatching of an immature egg. In an aspect, methods to control an arthropod lead to the death of larval forms of an arthropod. In some aspects, larval forms are more sensitive to exposure to PHPG than adult or nymph forms. Thus, in some aspects lower levels of PHPG may control immature forms of arthropods where the adult form is significantly less affected. In some aspects, PHPG is provided to a larval form to inhibit the metamorphosis of the larva. In an aspect, PHPG may be provided at sufficient levels to act as a larvacide. The present disclosure further provides for and includes methods of killing nymph forms of arthropods.

For many arthropods, exposure to PHPG leads to significant changes in behavior and PHPG acts as a very strong repellent. In some aspects, exposure to PHPG leads arthropods to search for an exit from the PHPG containing environment. In an aspect where the arthropod is unable to escape, the arthropod locates to a source of fresh (non-PHPG containing) air and attempts to survive. In household or non-experimental setting, such arthropods would exit the domicile or environment. Similarly, arthropods are repelled from entering environments that have even very low concentrations of PHPG. Thus the present disclosure provides for methods of controlling an arthropod by providing a PHPG containing environment and repelling insects, thereby blocking their entry.

In aspects according to the present disclosure, PHPG levels may be provided in excess over the amount necessary to kill a arthropod species. In such aspects, The control methods of the present disclosure are effective against almost every arthropod tested including examples from multiple phylogenetic orders and classes. The few arthropods that appear to be resistant to PHPG levels up to 0.6 ppm for 24 hours included adult cockroaches and tarantula spiders. PHPG is lethal to most species. Determining whether any specific species of arthropod is resistant or susceptible can be easily performed using the methods described below and known to one of skill in the art.

Certain arthropods are more susceptible to the methods of the present disclosure. Not to be limited by theory, flying insects, such as Diptera, are generally most susceptible due to high activity and rapid pumping of air containing hydrogen peroxide through their tracheal tubes. Accordingly, methods to control flying insects require lower levels of PHPG gas and are particularly suited to methods of control wherein the arthropod is repelled from the PHPG containing environment.

With respect to arachnids, those species having 'book lungs' are generally more susceptible than the tracheal tube systems of crawling insects. The present disclosure provides for and includes methods of controlling book lung containing arthropods including arachnids and scorpions.

In some aspects, larger arthropods appear to be more resistant to the killing effects of a PHPG environment. Not to be limited by theory, this may be the result of an increased diffusion distance to more sensitive portions of the arthropod body. Alternatively, the larger arthropod may be able to survive longer on stored oxygen once the tracheal system is closed off. In aspects according the present disclosure, resistance may be overcome by either increasing the length of time of the exposure, increasing the concentration of PHPG gas in the environment, or both.

It is understood that using the methods of the present disclosure and the knowledge of one of ordinary skill in the art, the particular effect on an arthropod may be readily determined. Further the level of PHPG necessary to kill, inhibit, or repel a given arthropod as well as the length of time necessary to kill, inhibit, or repel may be readily determined using the disclosed methods and knowledge known in the art.

Without being limiting, PHPG may be produced by a device for producing non-hydrated PHPG having an enclosure, an air distribution mechanism providing an airflow, a thin air-permeable substrate structure having a catalyst on its surface, and a source of light, where the airflow is through the air-permeable substrate structure and the device produces PHPG and directs it out of the enclosure when in operation. In some aspects, the source of light is a source of ultraviolet light. In some aspects, the airflow comprises an angle of incidence to the substrate structure that is greater than 45 degrees. In one aspect, the angle of incidence is 90 degrees. In another aspect, the airflow comprises air that has a humidity of at least 5%. In one aspect, the device further comprises a humidifier. The some aspects, the thin air-permeable substrate structure is between about 5 nm and about 750 nm thick. A more detailed explanation of a PHPG producing devices can be found in U.S. Pat. Nos. 8,168,122, 8,685,329, and U.S. Patent Application No. 61/988,535, the contents of all of which are herein incorporated in their entireties.

In aspects according to the present disclosure, a PHPG generating device may be incorporated into an air conditioner, a furnace, or a heating, ventilation, or an air-conditioning (HVAC) system.

The present disclosure provides for an includes a method for treating a house for an arthropod comprising providing PHPG to an environment within the house at a concentration of at least 0.05 ppm for a period of time, wherein the arthropod is controlled. In some aspects, the final PHPG concentration in said environment is at least 0.1 ppm. In other aspects, In other aspects, the final PHPG concentration in said environment is at least 0.2 ppm, least 0.4 ppm, least 0.6 ppm, or least 0.8 ppm. In one aspect, the final PHPG concentration in said environment is less than 1.0 ppm. In some aspects, the arthropod is selected from the group consisting of molds, mosquitoes, ants, termites, flies, moths, earwigs, crickets, centipedes, millipedes, roaches, and beetles. In one aspect, treating includes repelling from the PHPG containing environment or preventing entry into the PHPG containing environment by an arthropod selected from the group consisting of molds, mosquitoes, ants, termites, flies, moths, earwigs, crickets, centipedes, millipedes, roaches, and beetles. In another aspect, treating includes killing of an arthropod selected from the group consisting of molds, mosquitoes, ants, termites, flies, moths, earwigs, crickets, centipedes, millipedes, roaches, and beetles. In one aspect, the method includes killing mold in mold-prone areas such as basements, kitchens, and bathrooms. In one aspect, the method includes providing a relatively high concentration of PHPG for a period of time to kill an anthrop, followed by maintaining a lower concentration of PHPG to repel an arthropod from entering, or growing in an environment within the house. In one aspect, the method includes preventing mold from growing in mold-prone areas such as basements, kitchens, and bathrooms.

The present disclosure provides for and includes a method for controlling an arthropod in a storage facility. Storage facilities according to the present disclosure include personal and industrial storage facilities. In an aspect, the method includes providing a concentration of PHPG sufficient to repel flying insects. In an aspect, the methods include providing a concentration of PHPG sufficient to kill flying insects. In an aspect, the method includes providing a concentration of PHPG sufficient to prevent mold from growing within the storage facility. In an aspect, the methods include providing a concentration of PHPG sufficient to kill mold within the storage facility. In certain aspects, the PHPG is provided continuously to the storage facility. In other aspects, the PHPG is provided intermittently to the storage facility. In an aspect, the PHPG is provided during the daytime. In another aspect, the PHPG is provided during the overnight hours.

In aspects according the present disclosure, the PHPG for treating a storage facility is provided at a final concentration to a storage facility of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, least 0.6 ppm, least 0.7 ppm, least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm. Persons of ordinary skill in the art may readily determine a preferred level of PHPG in view of the current disclosure and further in view of the type, number, and source of the arthropod species.

The present disclosure provides for and includes a method for controlling an arthropod in a lodging facility comprising providing PHPG to an environment within the lodging facility at a concentration of at least 0.05 ppm for a period of time, where the arthropod population is controlled. Lodging facilities according to the present disclosure include but are not limited to hotels, motels, hostels, bed and breakfast facilities, tents, campers, and cottages. In an aspect, the method includes providing a concentration of PHPG sufficient to repel flying insects, fleas, mites, and lice. In an aspect, the methods include providing a concentration of PHPG sufficient to kill flying insects. In an aspect, the method includes providing a concentration of PHPG sufficient to repel bed bugs. In an aspect, the method includes providing a concentration of PHPG sufficient to prevent mold from growing within the lodging facility. In an aspect, the methods include providing a concentration of PHPG sufficient to kill flying insects, fleas, mites, and lice within the lodging facility. In an aspect, the methods include providing a concentration of PHPG sufficient to kill mold within the lodging facility. In an aspect, the methods include providing a concentration of PHPG sufficient to kill bed bugs within the lodging facility. In certain other aspects, the PHPG is provided continuously to the lodging facility. In other aspects, the PHPG is provided intermittently to the lodging facility. In an aspect, the PHPG is provided during the daytime. In another aspect, the PHPG is provided during the overnight hours. In one aspect, the PHPG is only provided when the lodging facility is unoccupied. In some aspects, the PHPG is produced by a stand-alone device. In other aspects, the PHPG is produced by a PHPG producing device that is incorporated into an air conditioner, a furnace, or a heating, ventilation, or an air-conditioning (HVAC) system.

In aspects according the present disclosure, the PHPG is provided to a lodging facility at a final concentration of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, least 0.6 ppm, least 0.7 ppm, least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm. Persons of ordinary skill in the art may readily determine a preferred level of PHPG in view of the current disclosure and further in view of the type, number, and source of the arthropod species.

The present disclosure provides for and includes a method for controlling an arthropod in a greenhouse. Greenhouses according to the present disclosure include personal and industrial greenhouse. In an aspect, the method includes providing a concentration of PHPG sufficient to repel flying insects. In an aspect, the methods include providing a concentration of PHPG sufficient to kill flying insects. In an aspect, the method includes providing a concentration of PHPG sufficient to prevent mold from growing within the greenhouse. In an aspect, the methods include providing a concentration of PHPG sufficient to kill mold within the greenhouse. In certain aspects, the PHPG is provided continuously to the greenhouse. In other aspects, the PHPG is provided intermittently to the greenhouse. In an aspect, the PHPG is provided during the daytime. In another aspect, the PHPG is provided during the nighttime.

In aspects according the present disclosure, the PHPG for treating a greenhouse is provided at a final concentration to a greenhouse of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, at least 0.6 ppm, at least 0.7 ppm, at least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm. Persons of ordinary skill in the art may readily determine a preferred level of PHPG in view of the current disclosure and further in view of the type, number, and source of the arthropod species.

The present disclosure provides for an includes a method treating a domesticated animal for the control of an arthropod comprising placing an animal in a PHPG containing environment for a period of time. In an aspect, the method includes providing a concentration of PHPG sufficient to repel ticks, fleas, mites, and lice. In another aspect, the methods include providing a concentration of PHPG sufficient to kill ticks, fleas, mites, and lice. In one aspect, the domesticated animal is selected from the group consisting of a cat, a dog, and a rodent.

In aspects according the present disclosure, the PHPG for treating a domesticated animal is provided at a final concentration to an environment for treating a domesticated animal of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, least 0.6 ppm, least 0.7 ppm, least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm. Persons of ordinary skill in the art may readily determine a preferred level of PHPG in view of the current disclosure and further in view of the type, number, and source of the arthropod species.

The present disclosure provides for an includes a method treating an animal for an arthropod parasite comprising placing an animal in a PHPG containing environment for a period of time. In some aspects, the final PHPG concentration in said PHPG containing environment is at least 0.05 parts per million. In other aspects, the final PHPG concentration in said PHPG containing environment is less than 1.0 ppm. In some aspects, the animals is left in said PHPG containing environment for a time period sufficient to control said arthropod. In as aspect of the method, said animal is a domestic pet. In one aspect, the domestic pet selected from the group consisting of a cat, a dog, or a rodent. In other aspects of the disclosure, the animal is a livestock animal. In some aspects, the livestock animal is selected from the group consisting of cattle, horses, sheep, goats, pigs, chickens, ducks, and geese. In one aspect, the arthropod is selected from the group consisting of ticks, horn flies, face flies, stable flies, biting lice, sucking lice, grubs and mites. In some aspects, the arthropod is a member of the phylogenetic class Mallophaga (chewing lice). In one aspect, the Mallophaga is selected from the group consisting of *Bovicola ovis* (sheep biting louse), *Menacanthus stramineus* (chicken body louse), and *Menopon gallinea* (common hen louse). In one aspect, the arthropod is selected from the group consisting shaft louse, wing louse, chicken head louse, northern fowl mite, red chicken mite, tropical fowl mite, fowl tick, and sticklight flea.

The present disclosure provides for and includes a method for controlling an arthropod in a food processing facility. In aspects according to the present disclosure, a food processing facility transforms a raw ingredients into food or food into processed forms. Food processing facilities according to the present disclosure include restaurants, food distribution centers, food packaging plants, rendering plants, abattoirs, fish canneries, and grocery stores. In an aspect, the method includes providing a concentration of PHPG sufficient to repel flying insects. In an aspect, the methods include providing a concentration of PHPG sufficient to kill flying insects. In certain aspects, the PHPG is provided continuously to the food processing facility. In other aspects, the PHPG is provided intermittently to the food processing facility. In an aspect, the PHPG is provided during working hours. In another aspect, the PHPG is provided during non-working hours.

In aspects according the present disclosure, the PHPG for the treatment of a food processing facility is provided at a final concentration to a food processing facility of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, least 0.6 ppm, least 0.7 ppm, least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm. Persons of ordinary skill in the art may readily determine a preferred level of PHPG in view of the current disclosure and further in view of the type, number, and source of the arthropod species.

The present disclosure provides for and includes a method for treating a house for a termite population comprising providing PHPG to an environment within the house at a concentration of at least 0.05 ppm for a period of time, wherein the termite population is controlled. In an aspect, the method includes providing a concentration of PHPG sufficient to repel termites. In an aspect, the methods include providing a concentration of PHPG sufficient to kill termites. In an aspect, the method includes providing a concentration of PHPG sufficient to cause the termites to cease eating. In certain aspects, the PHPG is provided continuously to the environment within the house. In other aspects, the PHPG is provided intermittently to the environment within the house. In an aspect, the PHPG is provided during the daytime. In another aspect, the PHPG is provided during the overnight hours.

In aspects according the present disclosure, the PHPG for the treatment of termites is provided at a final concentration to the environment within the house of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, least 0.6 ppm, least 0.7 ppm, least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm. Persons of ordinary skill in the art may readily determine a preferred level of PHPG in view of the current disclosure and further in view of the type, number, and source of the arthropod species.

The present disclosure provides for an includes a method for controlling an arthropod in cloths or linens during storage comprising providing PHPG to a storage container or package containing cloths or linens for a period of time. In an aspect, the method includes providing a concentration of PHPG sufficient to repel moths, flies, fleas, mites, and lice. In another aspect, the methods include providing a concentration of PHPG sufficient to kill moths, flies, ticks, fleas, mites, and lice. In one aspect, the cloths or linens are to be stored for the winter. In another aspect, the cloths or linens are to be stored for the summer. In certain aspects, the PHPG is provided continuously to the storage container or package. In other aspects, the PHPG is provided intermittently to the storage container or package. In one aspect, the PHPG is provided to the storage container or package at a desired concentration prior to sealing the storage container or package indefinitely.

In aspects according the present disclosure, the PHPG for controlling an arthropod in cloths or linens during storage is provided at a final concentration to cloths or linens of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, least 0.6 ppm, least 0.7 ppm, least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm. Persons of ordinary skill in the art may readily determine a preferred level of PHPG in view of the current disclosure and further in view of the type, number, and source of the arthropod species.

The present disclosure provides for and includes a method for controlling an arthropod in an agricultural product during shipping comprising providing PHPG to a shipping container containing an agricultural product to prepare a PHPG containing shipping container, shipping said container and maintaining said PHPG concentration at a predetermined concentration. In an aspect, the PHPG concentration is provided and maintained at a concentration of at least 0.05 parts per million (ppm). In one aspect, PHPG concentration is provided and maintained at a concentration of at least 0.1 ppm. In another aspect, the PHPG concentration is provided and maintained at a concentration of at least 0.2 ppm. In a further aspect, the PHPG concentration is provided and maintained at a concentration of at least 0.3 ppm. In a further aspect, the PHPG concentration is provided and maintained at a concentration of at least 0.4 ppm. In a further aspect, the PHPG concentration is provided and maintained at a concentration of at least 0.5 ppm, least 0.6 ppm, least 0.7 ppm, least 0.8 ppm, or at least 0.9 ppm. In one aspect, the PHPG concentration is provided and maintained at less than 1.0 ppm. In one aspect, the PHPG concentration is provided and maintained between 0.1 and 0.6 ppm. In another aspect, the PHPG concentration is provided and maintained between 0.4 and 1.0 ppm. In one aspect, the shipping container is continuously flushed with PHPG containing flushing gas. In one aspect, the PHPG containing flushing gas contains argon. Also included and provided for in the present disclosure are methods in which the PHPG is initially provided at concentration that is greater than the shipping concentration to provide enhanced initial killing of an arthropod. Using the methods below and those known in the art, determining the optimal amounts of PHPG during shipping may be accomplished with no more than routine experimentation.

In some aspects, the agricultural product for shipping under conditions for the control of an arthropod by PHPG is a fruit. In other aspects, the agricultural product is a vegetable. In other aspects, the agricultural product is a nut, a seed, or a meat. In some aspects, shipping containers are built to international standard making them interchangeable between shipping companies, rail and truck companies. In yet other aspects, the shipping containers may be optionally refrigerated, heated or otherwise treated as is standard during shipping. In aspects according to the present disclosure, the agricultural product shipped under conditions having PHGP is a banana. In an aspect the agricultural product is bulk coffee. In another aspect the agricultural product is soybean. In another aspect the agricultural product is a grain. In an aspect the grain is selected from the group consisting of rice, wheat, corn, and barley. In another aspect the agricultural product is a perishable product. In certain aspects, the agricultural product is shipped in an environment having PHPG to minimize or avoid the transport and introduction of foreign species.

The present disclosure provides for, and includes, methods for the control of a member of the phylum Arthropoda. In an aspect, the arthropod may be a part of a population. In certain aspects, a population of arthropods may include members at a variety of stages of development including without limitation eggs, larva, pupae, nymphs, and adults. In other aspects according to the present disclosure, the controlled arthropods may be part of a mixed population comprising two or more different populations of arthropods. Sources of detailed phylogenetic, behavioral, and physical characteristics are known to those of skill in the art. For example on the internet at insects.tamu.edu, and bugguide.net.

In some aspects, the eggs may be mature, immature, fertilized or unfertilized. In some aspects, the larva may be at various stages of development. In some aspects, the nymphs may be at any stage of development.

In another aspect, the present disclosure provides for and includes methods for the control of arthropods that are members of the phylogenetic order Homoptera. Members of the order Homoptera that may be controlled according to the methods of the present disclosure include, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Phydloxera vastatrix, Pemphigus* spp. *Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

In another aspect, the present disclosure provides for and includes methods for the control of arthropods that are members of the phylogenetic order Lepidoptera. Members of the order Lepidoptera that may be controlled according the methods of the present disclosure include, for example, *Pectinophora gossypiella, Bupalus piniarius, Chemiatobia brumata, Lithocolletis blancardclia, Hyponomeuta padella, Plutella maculipennis, Malacosoma neustria, Euproctis chrysorrhoea, Lynmantria* spp., *Bucculatrix thurberiella, Phyllocnistis citrella, Agrotis* spp. *Euxoa* spp., *Feltia* spp., *Earias insulana, Heliothis* spp., *Spodoptera exigua, Mamestra brassicae, Panolis flammea, Prodenia litura, Spodoptera litura, Spodoptera* spp., *Trichoplusia ni, Carpocapsa pomnonella, Pieris* spp., *Chilo* spp., *Pyrausta nubilalis, Ephestia kuehniella, Glalleria mellonella, Tineola bisselliella, Tinea pellionella, Hofmannophila pseudospretella, Cacoccia podana, Capua reticulana, Choristoneura fiuniferana, Clysia ambiguella, Homona magnanima* and *Tortrix viridana*.

In another aspect, the present disclosure provides for and includes methods for the control of arthropods that are members of the phylogenetic order Coleoptera. Members of the order Coleoptera that may be controlled according the methods of the present disclosure include, for example, *Anobium punctatum, Rhizopertha dominica, Bruchidius obtectus, Acanthoscelides obtectus, Hylotrupes bajulus, Agelastica alni, Leptinotarsa decemlincata, Phaedon cochleariae, Diabrotica* spp., *Psylliodes chrysocephala, Epilachna varivestis, Atomaria* spp., *Oryzaephilus surinamnensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus. Ptinus* spp., *Niptus hololeucus, Gibbium psylloides, Tribolium* spp. *Tenebrio molitor, Agriotes* spp., *Conoderus* spp., *Melolontha melolontha, Amphimallon solstitialis* and *Costelytra zealandica*.

In another aspect, the present disclosure provides for and includes methods for the control of arthropods that are members of the phylogenetic order Coleoptera. Members of the order Coleoptera that may be controlled according the methods of the present disclosure include, for example, *Acalymma vittatum, Acanthoscelides obtectus, Adoretus* spp., *Agelastica alni, Agriotes* spp., *Alphitobius diaperinus, Amphimallon solstitialis, Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lisso-rhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sphenophorus* spp., *Stegobium paniceum*, *Sternechus* spp., *Symphyletes* spp., *Tanymecus* spp., *Tenebrio molitor*, *Tribolium* spp., *Trogoderma* spp., *Tychius* spp., *Xylotrechus* spp., and *Zabrus* spp.

In another aspect, the present disclosure provides for and includes methods for the control of arthropods that are members of the phylogenetic class Arachnida. Members of the class Arachnida that may be controlled according the methods of the present disclosure include, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Centruroides* spp., *Chorioptes* spp., *Dermanyssus gallinae*, *Dermatophagoides pteronyssius*, *Dermatophagoides farinae*, *Dermacentor* spp., *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vaejovis* spp., and *Vasates lycopersici*.

In another aspect, the present disclosure also provides for and includes methods to control arthropods that are Coleoptera (beetles). A non-exhaustive list of these arthropods includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass *Ataenius*), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata*, *Cerosterna* spp., *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage *curculio*), *Chaetocnema* spp. (chrysomelids), *Colaspis* spp. (soil beetles), *Conoderus scalaris*, *Conoderus stigmosus*, *Conotrachelus nenuphar* (plum *curculio*), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae*, *Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus*, *Liogenys suturalis*, *Lissorhoptrus oryzophilus* (rice water weevil), *Lyctus* spp. (wood beetles/powder post beetles), *Maecolaspis joliveti*, *Megascelis* spp., *Melanotus communis*, *Meligethes* spp., *Meligethes aeneus* (blossom beetle), *Melolontha melolontha* (common European cockchafer), *Oberea brevis*, *Oberea linearis*, *Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae*, *Pantomorus* spp. (weevils), *Phyllophaga* spp. (May/June beetle), *Phyllophaga cuyabana*, *Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

The present disclosure provides for and includes methods to control arthropods that are members of the subphylum Myriapoda. Members of the subphylum Myriapoda that may be controlled according the methods of the present disclosure include, for example, a member of the class Diplopoda or Chilopoda.

In another aspect, the present disclosure also provides for and includes methods to control arthropods that are members of the subphylum Hexapoda. The present disclosure also provides for and includes methods to control arthropods that are members of the phylogenetic Class Insecta.

In another aspect, the present disclosure also provides for and includes methods to control arthropods that are Dermaptera (earwigs).

In another aspect, the present disclosure also provides for and includes methods to control arthropods that are Dictyoptera (cockroaches). A non-exhaustive list of these pests includes, but is not limited to, *Blattella germanica* (German cockroach), *Blatta orientalis* (oriental cockroach), *Parcoblatta pennylvanica*, *Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In aspects according to the present disclosure, the effective level of PHPG to control Dictyoptera is greater than 0.6 ppm. In certain aspects, the effective level of PHPG to control Dictyoptera is greater than 1.0 ppm. Yet other aspects, of PHPG to control Dictyoptera is greater than 1.5 ppm. Adult Dictyoptera appear to be resistant to low levels of PHPG and appear unaffected, however, eggs, larva and immature forms are expected to be susceptible to PHPG. In certain aspects, the present disclosure provides for and induces methods for controlling Dictyoptera that provides for the arthropodicide of immature Dictyoptera, while altering the behavior of adult Dictyoptera. In an aspect, PHPG provides for the prevention of infestation by adult Dictyoptera by inhibiting the infiltration of adult Dictyoptera into a PHPG treated space.

In another aspect, the present disclosure also provides for and includes methods to control arthropods that are Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (*Mediterranea* fruit fly), *Chrysops* spp. (deer flies), *Cochliomyia* spp. (screwworms), *Contarinia* spp. (gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae*, *Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

Yet other examples of arthropods that are members of the class Diptera that can be controlled by the methods provided for in the present disclosure include, but are not limited to *Asphondylia* spp., *Bibio hortulanus*, *Calliphora erythrocephala*, *Chironomus* spp., *Chrysomyia* spp., *Cordylobia anthropophaga*, *Culicoides* spp., *Culiseta* spp., *Cuterebra* spp., *Dacus oleae*, *Dermatobia hominis*, *Echinocnemus* spp., *Glossina* spp., *Haematopota* spp., *Hydrellia* spp., *Hyppobosca* spp., *Hypoderma* spp., *Lucilia* spp., *Lutzomia* spp., *Mansonia* spp., *Nezara* spp., *Oestrus* spp., *Pegomyia* spp., *Phlebotomus* spp., *Phormia* spp., *Prodiplosis* spp., *Rhagoletis* spp., *Sarcophaga* spp., *Simulium* spp, *Stomoxys* spp., *Tannia* spp., and *Tetanops* spp.

In another aspect, the present disclosure also provides for and includes methods to control arthropods that are Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus*, *Dichelops furcatus*, *Dysdercus suturellus* (cotton stainer), *Edessa meditabunda*, *Eurygaster maura* (cereal bug), *Euschistus heros*, *Euschistus servus* (brown stink bug), *Helopeltis antonii*, *Helopeltis theivora* (tea blight plantbug), *Lagynotomus* spp. (stink bugs), *Leptocorisa oratorius*, *Leptocorisa varicornis*, *Lygus* spp. (plant bugs), *Lygus hesperus* (western tarnished plant bug), *Maconellicoccus hirsutus*, *Neurocolpus longirostris*, *Nezara viridula* (southern green stink bug), *Phytocoris* spp. (plant bugs), *Phytocoris californicus*, *Phytocoris relativus*, *Piezodorus guildingi*, *Poecilocapsus lineatus* (fourlined plant bug), *Psallus vaccinicola*, *Pseudacysta perseae*, *Scaptocoris castanea*, and *Triatoma* spp. (bloodsucking conenose bugs/kissing bugs).

Yet other examples of pests that are members of the class Heteroptera and can be controlled by the methods provided for in the present disclosure include, but are not limited to *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Rhodnius* spp., *Sahlbergella singularis*, *Scotinophora* spp., *Stephanitis nashi*, and *Tibraca* spp.

In another aspect, the present disclosure also provides for and includes methods to control arthropods that are Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses*, *Aleurothrixus floccosus* (woolly whitefly), *Aluacaspis* spp., *Amrasca bigutella bigutella*, *Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii*, *Bemisia tabaci* (sweetpotato whitefly), *Brachycolus noxius* (Russian aphid), *Brachycorynella asparagi* (asparagus aphid), *Brevennia rehi*, *Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata*, *Metopolophium dirhodum* (rose grain aphid), *Mictis longicornis*, *Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (whitebacked planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

Yet other examples of pests that are members of the class Homoptera that can be controlled by the methods provided for in the present disclosure include, but are not limited to *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pini*, *Arboridia apicalis*, *Aspidiella* spp., *Aspidiotus* spp. *Atanus* spp., *Brachycaudus helichrysii*, *Brachycolus* spp., *Brevicoryne brassicae*, *Calligypona marginate*, *Carneocephala fulgida*, *Ceratovacuna lanigera*, *Cercopidae*, *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Lecanium* spp., *Lipaphis erysimi*, *Mahanarva* spp., *Melanaphis sacchari*, *Metcalfiella* spp., *Monellia costalis*, *Monelliopsis pecanis*, *Myzus* spp., *Nasonovia ribisnigri*, *Oncometopia* spp., *Orthezia praelonga*, *Parabemisia myricae*, *Paratrioza* spp., *Parlatoria* spp., *Pemphigus* spp., *Phenacoccus* spp., *Phloeomyzus passerinii*, *Phorodon humuli*, *Phylloxera* spp., *Pinnaspis aspidistrae*, *Protopulvinaria pyriformis*, *Pseudaulacaspis pentagona*, *Psylla* spp., *Pteromalus* spp., *Pyrilla* spp., *Quadraspidiotus* spp., *Quesada gigas*, *Rastrococcus* spp., *Scaphoides titanus*, *Selenaspidus articulatus*, *Sogata* spp., *Sogatodes* spp., *Stictocephala festina*, *Tenalaphara malayensis*, *Tinocallis caryaefoliae*, *Tomaspis* spp., *Trialeurodes* spp., *Trioza* spp., *Typhlocyba* spp., *Viteus vitifolii*, and *Zygina* spp.

In another aspect, the present disclosure also provides for and includes methods to control arthropods that are Hymenoptera (ants, wasps, and bees). A non-exhaustive list of these pests includes, but is not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another aspect, the present disclosure also provides for and includes methods to control arthropods that are Isoptera (termites). A non-exhaustive list of these pests includes, but is not limited to, *Coptotermes* spp., *Coptotermes curvignathus*, *Coptotermes frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In another aspect, the present disclosure also provides for and includes methods to control arthropods that are Lepidoptera (moths and butterflies). A non-exhaustive list of these pests includes, but is not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruit tree leafroller), *Archips rosana* (rose leaf roller), *Argyrotaenia* spp. (tortricid moths), *Argyrotaenia citrana* (orange *tortrix*), *Autographa gamma*, *Bonagota cranaodes*, *Borbo cinnara* (rice leaf folder), *Bucculatrix thurberiella* (cotton leaf perforator), *Caloptilia* spp. (leaf miners), *Capua reticulana*, *Carposina niponensis* (peach fruit moth), *Chilo* spp., *Chlumetia transversa* (mango shoot borer), *Choristoneura rosaceana* (oblique banded leaf roller), *Chrysodeixis* spp., *Cnaphalocerus medinalis* (grass leafroller), *Colias* spp., *Conpomorpha cramerella*, *Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta*, *Diaphania* spp. (stem borers), *Diatraea* spp. (stalk borers), *Diatraea saccharalis* (sugarcane borer), *Diatraea graniosella* (southwestern corn borer), *Earias* spp. (bollworms), *Earias insulata* (Egyptian bollworm), *Earias vitella* (rough northern bollworm), *Ecdytopopha aurantianum*, *Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema*, *Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant *tortrix*), *Pandemis heparana* (brown apple *tortrix*), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabs*, *Plodia interpunctella* (Indian meal moth), *Plutella xylostella* (diamondback moth), *Polychrosis viteana* (grape berry moth), *Prays endocarps*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia inferens* (pink rice stem borer), *Sesa-*

*mia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera frugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

Yet other examples of pests that are members of the class Lepidoptera that can be controlled by the methods provided for in the present disclosure include, but are not limited to *Acronicta major, Aedia leucomelas, Alabama* spp., *Anarsia* spp., *Anticarsia* spp., *Argyroploce* spp., *Barathra brassicae, Borbo cinnara, Bupalus piniarius, Busseola* spp., *Cacoecia* spp., *Caloptilia theivora, Carpocapsa pomonella, Chematobia brumata, Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Eldana saccharina, Epinotia* spp., *Epiphyas postvittana, Etiella* spp., *Eulia* spp., *Euproctis* spp., *Euxoa* spp., *Galleria mellonella, Gracillaria* spp., *Grapholitha* spp., *Hedylepta* spp., *Hofmannophila pseudospretella, Homoeosoma* spp., *Homona* spp., *Hyponomeuta padella, Kakivoria flavofasciata, Laphygma* spp., *Laspeyresia molesta, Leucoptera* spp., *Lithophane antennata, Lobesia* spp., *Lymantria* spp., *Lyonetia* spp., *Malacosoma neustria, Mamestra brassicae, Mocis* spp., *Myth imna separata, Nymphula* spp., *Oiketicus* spp., *Oria* spp., *Orthaga* spp., *Ostrinia* spp., *Oulema oryzac, Panolis flammea, Parnara* spp., *Pectinophora* spp., *Perileucoptera* spp., *Phthorimaea* spp., *Pieris* spp., *Platynota stultana, Plusia* spp., *Prays* spp., *Prodenia* spp., *Protoparce* spp., *Pyrausta nubilalis, Schoenobius* spp., *Scirpophaga* spp., *Scotia segetum, Sparganothis* spp., *Stathmopoda* spp., *Stomopteryx subsecivella, Tecia solanivora, Tinea pellionella, Tortrix* spp., *Trichophaga tapetzella, Trichoplusia* spp., and *Virachola* spp.

In another aspect, the present disclosure also provides for and includes methods to control arthropods that are Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen louse).

In another aspect, the present disclosure also provides for and includes methods to control arthropods that are Orthoptera (grasshoppers, locusts, and crickets). A non-exhaustive list of these pests includes, but is not limited to, *Anabrus simplex* (Mormon cricket), Gryllotalpidae (mole crickets), *Locusta migratoria, Melanoplus* spp. (grasshoppers), *Microcentrum retinerve* (angular winged katydid), *Pterophylla* spp. (katydids), *chistocerca gregaria, Scudderia furcata* (fork tailed bush katydid), and *Valanga nigricorni.*

In another aspect, the present disclosure also provides for and includes methods to control arthropods that are Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another aspect, the present disclosure also provides for and includes methods to control arthropods that are Siphonaptera (fleas). A non-exhaustive list of these pests includes, but is not limited to, *Ctenocephalides canis* (dog flea), *Ctenocephalides felis* (cat flea), and *Pulex irritans* (human flea).

In another aspect, the present disclosure also provides for and includes methods to control arthropods that are Thysanoptera (*thrips*). A non-exhaustive list of these pests includes, but is not limited to, *Frankliniella fusca* (tobacco *thrips*), *Frankliniella occidentalis* (western flower *thrips*), *Frankliniella shultzei Frankliniella williamsi* (corn *thrips*), *Heliothrips haemorrhaidalis* (greenhouse *thrips*), *Riphiphorothrips cruentatus, Scirtothrips* spp., *Scirtothrips citri* (citrus *thrips*), *Scirtothrips dorsalis* (yellow tea *thrips*), *Taeniothrips rhopalantennalis*, and *Thrips* spp.

In another aspect, the present disclosure also provides for and includes methods to control arthropods that are Thysanura (bristletails). A non-exhaustive list of these pests includes, but is not limited to, *Lepisma* spp. (silverfish) and *Thermobia* spp. (firebrats).

In another aspect, the present disclosure also provides for and includes methods to control arthropods that are Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (American dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (two-spotted spider mite), and *Varroa destructor* (honey bee mite).

Additional information regarding arthropods suitable for control using the methods of the present disclosure, may be found in "Handbook of Pest Control—The Behavior, Life History, and Control of Household Pests" by Arnold Mallis, 9th Edition, copyright 2004 by GIE Media Inc.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. For example, methods of using PHPG gas to kill arthropods are also effective at repelling arthropods. Thus, following the initial killing of an arthropod, continued use of PHPG prevents the reinfestation.

Various embodiments and aspects of the present invention as delineated hereinabove and as claimed in the claims section below find experimental support in the following Examples. The following Examples are presented for the purposes of illustration and should not be construed as limitations.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

EXAMPLES

Example 1

Generation and Measurement of PHPG

All PHPG concentration readings take place with Draeger products. A Pac III, Polytron 7000 or Draeger Tubes are utilized in all tests, generally according to manufacturer's instructions. The Polytron displays a digital reading when air is drawn through the mesh sensor. Most commonly, Draeger Tubes are used after clipping on both ends and placement in a ACCURO™ Pump. Per manufacturer instructions, the tubes are pumped 100 times and the level of PHPG determined by observing the color change in the crystals. The PAC III has proved to be generally less effective in measuring very low levels of PHPG.

Example 2

Laboratory Testing of PHPG for the Control of Arthropod Species

The effects of Purified Hydrogen Peroxide Gas (PHPG) on selected arthropod species is performed to determine the efficacy on controlling an arthropod using the indirect dispersion of PHPG in a space. In these experiments, the knockdown and mortality rates in mosquitoes, bed bugs, termites, ants, moths, house flies, and spiders is assessed.

Black wood ants, house flies (adult and pupae), large saturniid moths, termites (soldier and living), and cellar spiders are obtained from Carolina Supplies and shipped overnight. All organisms are fed prior to shipping from Carolina Supplies. Bed bugs and mosquitoes are sourced locally due to government shipping restrictions. The test samples are stored in a cabinet at ambient temperature and humidity until use in the study. The samples are labeled and color-coded for easy identification. In certain experiments, specimens of wild caught arthropods are used in the controlled experiments, including for example Brazilian cockroaches.

All testing is conducted in a sealed, Static Dissipative PVC chamber, Terra Universal (Fullerton, Calif.) Model 3305-10F: 59 inches W×24 inches D×25 inches H. With additional airlock Terra Universal Model 1680-81B 11.5 inches W×10 inches D×10.5 inches H. Arthropods are placed inside transfer containers (pint size paper containers). The top and bottom diameters of these containers are 3.75 and 2.87 inches respectively with a height of 3.5 inches. All arthropods are released once the airlock is sealed. Arthropods are allowed to recover following PHPG exposure and observed in 8 oz glass Pyrex® (Tewksbury, Mass.) containers with sealed glass lids.

Three replicates of ten of each arthropod are subjected to PHPG. An additional three replicates are subjected to a non PHPG producing device and serve as untreated controls. The arthropods are observed for knockdown at 0.5, 1, 2, 3, 4, 5, and 15 minutes. Mortality counts are taken after 24 hours of PHPG exposure. If at 24 hours mortality is less 90%, additional readings are taken following 48 hours of PHPG exposure. The test samples are exposed to the test environment containing PHPG until a 90% knockdown is achieved. The test samples are provided PHPG emitted from a PHPG producing device in the center of the test chamber. Time frames are recorded for each replicate. Just prior to treatment the arthropods are transferred into the transfer containers. Forty eight hours after treatment, they are removed from the treatment chamber and transferred to recovery containers and covered with screened lids for observation.

After treatment, the arthropods are observed for knockdown and mortality at 0.5, 1, 2, 3, 4, 5, 15, 30 minutes and 1, 2, 3, 4, 5, 10, 15, 24, and 48 hours. Knockdown occurs when an arthropod cannot right itself when placed on its back but is still able to move at least one body part. The arthropods are then transferred from the treatment chamber to recovery containers. Another knockdown/mortality observation is made 15 minutes later.

If all ten arthropods are recorded as knocked down or deceased during any observation before 15 minutes have elapsed, subsequent observations are not made. Mortality counts are made at 24 hours, and 48 hours or sooner (if applicable). All dead arthropods are confirmed by probing or agitation to make sure that they are unable to move (any that show movement visible to the naked eye are recorded as moribund). Arthropods that can crawl or right themselves when placed on their backs are recorded as being alive.

After the knockdown counts are complete, the arthropods are maintained in the laboratory at ambient temperature and humidity conditions with a normal 8:16 light:dark cycle for 24 hours. Additional mortality readings are taken at 48 hours if less than 90% mortality is recorded at 24 hours. A 48 hour reading depends upon control mortality remaining less than 10%. Temperature and humidity are recorded in the treatment area, and in the laboratory where the arthropods are subsequently held for the duration of the test. The number of dead arthropods per replicate are added together for a total mortality count. Abbott's Formula is used to correct for any mortality among the controls. The results are presented in Table 1.

TABLE 1

Effect of PHPG on Arthropod Species in Laboratory Tests

| Organism | PHPG Level | Exposure Time | Attempt to Flee? | Percent Killed | Observations |
| --- | --- | --- | --- | --- | --- |
| Bedbugs | 0.6 ppm | 3 hours 60 hours | No, Went Dormant | 50% 100% | All bedbugs reacted within fifteen seconds. Bedbugs with recent blood meal regurgitated. Females immediately laid immature eggs. Immature eggs immediately hatched. Nymphs died in seconds. |

TABLE 1-continued

Effect of PHPG on Arthropod Species in Laboratory Tests

| Organism | PHPG Level | Exposure Time | Attempt to Flee? | Percent Killed | Observations |
|---|---|---|---|---|---|
| | | | | | Almost all bedbugs then stopped moving. Bedbugs that had regurgitated recent blood meal remained active, collecting and stacking dormant bedbugs. Dormant bedbugs began to revive when removed from the environment after one hour, and were replaced. All died over time. |
| Brown Dog Tick | 0.6 ppm | 3 hours 60 hours | Yes | 70% 100% | All ticks searched for an exit until they succumbed. |
| Carpenter Ants | 1.0 ppm | 24 Hours | Yes | 15% | All ants attempted to flee. When unable 50% collected in areas where fresh air was seeping into the chamber and remained inactive. Others continued to search for an exit. Smallest ants died first. |
| Cockroaches | 0.6 ppm | 24 Hours | No | 0% | Appeared resistant at low level of PHPG. Did not react to the gas, suggesting possession of protective enzymes. |
| Cellar Spiders | 1.0 ppm | 24 Hours | Yes | 33% | Smallest spiders died within one hour. Larger spiders survived long enough to find a fresh air source. |
| Deer Ticks | 0.6 ppm | 3 hours 60 hours | Yes | 70% 100% | All ticks searched for an exit until they succumbed. |
| Fruit Flies | 0.3 ppm | 72 hours | Not noted | 100% | |
| House Fly Pupae | 0.5 ppm | 7 days | N/A | 100% | 100 pupae expected to hatch within 3 days. Did not hatch at all within one week. |
| Tarantula | 0.6 ppm | 24 hours | No | 0% | Appeared resistant. Did not react to the gas, suggesting possession of protective enzymes. |
| Termites | 0.1 ppm | 24 hours | Yes, Then went dormant | 100% | Very low exposure caused the termites to cease activity and seek shelter, where they went dormant. Larger concentrations should kill. |
| Wolf Spiders | 1.0 ppm | 1 hour | Yes | 100% | Very susceptible; and general observation |

Example 3

Real World Testing of PHPG for the Control of Arthropod Species

In November 2012, the effects of PHPG gas treatment according to the present disclosure was performed on a 1400 sq ft Pool House that had not been maintained for years. Prior to testing, the primary function was for storage and the very occasional guest. Window seals were cracked and therefore air leakage throughout the space was increased. Initially there was some mold present on the wall with an "in window" air conditioning unit. Prior to the initiation of testing, the space itself was cleared out and swept clean. No chemicals or cleaners were used at any time in this space for weeks prior to testing. There was no cleaning or dusting of the exposed rafters, kitchen cabinets, drawers, closets or the HVAC system that was not operational for years. A space heater was included to maintain the temperature above 60 degrees ° F. Two 14"×12" by 12" PHPG generating devices comprising a filters, fan, bulb, and a PHPG generating sail (See, U.S. Pat. Nos. 8,168,122, 8,685,329, and U.S. Patent Application No. 61/988,535). Two PHPG generating devices were placed in the space for an initial cleansing and to establish levels. After 27 hours, 109 arthropods were confirmed dead including crickets, ants, spiders, and house flies. The majority of the kills happened around the outer walls of the space with limited kills in the interior portions of the space. Observed concentration of PHPG, measured as provided in Example 1, at 27 hours was 0.4 ppm. No live insects were observed.

The effects of PHPG treatment of human lice was observed. After installing a PHPG generating device, the child subject reported the end of itching within one hour. All signs of lice were eliminated and lice free within two days of the initiation of treatment.

Additional observations of the effects of PHPG treatment of arthropod species was observed during the development of PHPG generating devices for the control of molds, bacteria, and viruses. The results and observations of these species is presented in Table 2

TABLE 2

Observations on Arthropod Species in Real World Tests

| Organism | PHPG Level | Exposure Time | Attempt to Flee? | Percent Killed | Observations |
|---|---|---|---|---|---|
| Crickets | 0.4 ppm | 21 hours | Yes | 100% | Test conducted in Garden house. Tried to exit through HVAC Vents. |
| House Flies | 0.2 ppm | 24 hours | Yes | 100% | Flies exhibited frantic behavior and disorientation within 30 minutes. First deaths within one hour. All died within day. TESTINg pupa |
| Lice and nits | 0.2 ppm | 2 days | N/A | 100% | Infested child reported end of itching within one hour. Bedding and other exposed items fully treated within two days. |
| Mosquitoes | 0.2 ppm | 2 hours | Yes | 100% | All mosquitoes that entered the environment immediately began searching for an exit, became disoriented, frantic, and then died within a couple of hours. |
| Stink Bugs | 0.3 ppm | 24 hours | Yes | 100% | Many dead bugs found around device. |
| Yellow Jackets and Nest | 0.3 ppm | 1 day | Yes | 100% | Test in attack where nest was hatching. All yellow jackets died and unhatched yellow jackets in the nest died. |

What is claimed:

1. A method for controlling an arthropod in a food processing facility comprising providing Purified Hydrogen Peroxide Gas (PHPG) at a concentration of at least 0.1 parts per million (ppm) to about 5.0 ppm and comprising 0.015 ppm ozone or less to a food processing facility.

2. The method of claim 1, wherein said food processing facility is selected from the group consisting of a restaurant, a food distribution center, a food packaging plant, a rendering plant, an abattoir, a fish cannery, and a grocery store.

3. The method of claim 1, wherein said PHPG is provided continuously.

4. The method of claim 1, wherein said arthropod is a member of the phylogenetic class selected from the group consisting of Insecta, Arachnida, Diplopoda, and Chilopoda.

5. The method of claim 1, wherein said arthropod is a member of a phylogenetic order selected from the group consisting of Collembola (e.g., spring tails), Thysanura (e.g., silverfish, firebrats, bristletails), Ephemeroptera (e.g., mayflies), Odonata (e.g., dragonflies, damselflies), Phasmida (e.g., walking sticks), Orthoptera (e.g., crickets, katydids, grasshoppers), Mantodea (e.g., praying mantis), Blattaria (e.g., cockroaches), Isoptera (e.g., termites), Dermaptera (e.g., earwigs), Plecoptera (e.g., stonefly), Psocoptera (e.g., psocids "barklice"), Phthiraptera (e.g., lice including Mallophaga and Anoplura), Hemiptera (e.g., true bugs; waterbug, chinch bug, Reduviidae; stink bugs), Homoptera (e.g., aphids, cicadas), Thysanoptera (e.g., *thrips*), Neuroptera (e.g., doodle bugs, antlions, lacewings), Coleoptera (e.g., beetles, weevils), Mecoptera (e.g., scorpion flies), Siphonaptera (e.g., fleas), Diptera (e.g., flies, mosquitos, midges), Trichoptera (e.g., caddisflies), Lepidoptera (e.g., bollworm, armyworms, cutworms, codling moth, clothes moth and cabbageworm including immature forms of "caterpillers"), Hymenoptera (e.g., ants, bees, wasps, hornets, yellow jackets, sawflies), Scorpionida (e.g., scorpions), Uropygi (e.g., vinegaroon), and Araneae (e.g., spiders, tarantula).

6. The method of claim 1, wherein said arthropod is selected from the group consisting of: an ant (Formicidae), waterbug (Nepomorpha), a palmetto bug (Battidae), Florida woods cockroach (*Eurycotis floridana*), a bed bug (*Cimex* spp.); an assassin bug (Reduviidae), a hornet (Vespinae), a wasp (Vespidae), a mud dauber (Apoidea), a yellow jacket (Vespinae), an aphid (Aphididae), a caterpillar (Lepidoptera larva), a cut worm (Noctuidae larva), an earwig (Dermaptera), a termite (Termitoidae), a fly (*Musca* spp.), a gypsy moth larvae or adult (*Lymantria* spp.), a Japanese beetle (*Popillia* spp.), a carpet beetle (Bostrichoidea), a leafhopper (Cicadellidae), a millipede (Diplopoda), a red spider mite (Tetranychinae), a webworm (Crambini), a whitefly (Aleyrodidae), a firebrat (*Lepsima* spp.), a non-biting gnat (*Sylvicola* spp.), a pillbug (Isopoda), a boxelder bug (*Contarinia* spp.), a centipede (*Hemiscolopendra* spp.), a cricket (*Oecanthus* spp., *Gryllidea* spp., *Gryllus* spp., and *Daihinia* spp.), a flea (*Siphonaptera, Pulicidae* spp.), a fruit fly (Acalyptratae), a gnat (Bibionomorpha), a ground beetle (Harpalitae), a mosquito (Culicidae), a louse (Phthiraptera, Anoplura, Mallophaga), a scorpion (Scorpiones), a silverfish (Zygentoma), a sowbug (Oniscidae), a stink bug (Pentatomidae), a tick (*Ixodidae, Ixodes* spp. and *Rhipicephalus* spp.), and including eggs and larval forms of each.

7. The method of claim 1, wherein said provided PHPG is prepared from ambient air having a relative humidity of between 5% and 99%.

8. The method of claim 1, wherein said PHPG containing environment comprises a PHPG concentration of between 0.1 parts-per-million (ppm) and 1.5 ppm.

9. The method of claim 1, wherein said PHPG is provided to said environment by a PHPG generating device that is a stand-alone device or is a component of a climate control system.

10. The method of claim 1, wherein said food processing facility is an abattoir and said arthropod is a member of the order Diptera.

11. The method of claim 1, wherein said food processing facility is a food packaging plant and said arthropod is a member of the order Diptera.

12. The method of claim 1, wherein said food processing facility is a rendering plant and said arthropod is a member of the order Diptera.

13. The method of claim 1, wherein said food processing facility is a fish cannery and said arthropod is a member of the order Diptera.

14. The method of claim 1, wherein said food processing facility is a grocery store and said arthropod is a member of the order Diptera.

15. The method of claim 1, wherein said food processing facility is an abattoir and said arthropod is a member of the order Hymenoptera.

16. The method of claim 1, wherein said food processing facility is a food packaging plant and said arthropod is a member of the order Hymenoptera.

17. The method of claim 1, wherein said food processing facility is a rendering plant and said arthropod is a member of the order Hymenoptera.

18. The method of claim 1, wherein said food processing facility is a fish cannery and said arthropod is a member of the order Hymenoptera.

19. The method of claim 1, wherein said food processing facility is a grocery store and said arthropod is a member of the order Hymenoptera.

* * * * *